United States Patent
Pekar et al.

(10) Patent No.: US 7,708,682 B2
(45) Date of Patent: May 4, 2010

(54) METHOD AND DEVICE FOR PLANNING A RADIATION THERAPY

(75) Inventors: Vladimir Pekar, Hamburg (DE); Michael R. Kaus, Hamburg (DE); Todd McNutt, Verona, WI (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1072 days.

(21) Appl. No.: 10/573,730

(22) PCT Filed: Sep. 10, 2004

(86) PCT No.: PCT/IB2004/051739

§ 371 (c)(1),
(2), (4) Date: Mar. 28, 2006

(87) PCT Pub. No.: WO2005/031629

PCT Pub. Date: Apr. 7, 2005

(65) Prior Publication Data

US 2007/0049785 A1    Mar. 1, 2007

Related U.S. Application Data

(60) Provisional application No. 60/506,972, filed on Sep. 29, 2003, provisional application No. 60/584,833, filed on Jun. 30, 2004.

(51) Int. Cl.
*A61N 5/00* (2006.01)
(52) U.S. Cl. .......................... 600/1; 382/131; 382/173
(58) Field of Classification Search .................. 600/1–8
See application file for complete search history.

(56) References Cited

U.S. PATENT DOCUMENTS

| 6,169,817 | B1 | 1/2001 | Parker et al. ................. 382/131 |
| 2003/0036083 | A1 | 2/2003 | Tamez-Pena et al. ............ 435/6 |
| 2003/0072479 | A1 | 4/2003 | Totterman et al. ............ 382/131 |
| 2003/0125622 | A1 | 7/2003 | Schweikard et al. ........ 600/437 |

FOREIGN PATENT DOCUMENTS

DE    198 29 170 C2    1/2000

OTHER PUBLICATIONS

Birkner, M., et al.; Adapting inverse planning to patient and organ geometrical variation: algorithm and implementation; 2003; Med. Phys.; 30(10)2822-2831.
Brock, K.K., et al.; Inclusion of organ deformation in dose calculations; 2003; Med. Phys; 30(3)290-295.
Liang, J., et al.; Reducing uncertainties in volumetric image based deformable organ Registration; 2003; Med. Phys; 30(8)2116-2122.
Weese, J., et al.; Shape Constrained Deformable Models for 3D Medical Image Segmentation; 2001; Springer-Verlag; LNCS 2082; pp. 380-387.
Yan, Di, et al.; A Model to Accumulate Fractionated Dose in a Deforming Organ; 1999; Int.J.Radiation Oncology Biol. Phys.; 44(3)665-675.
Yan, Di, et al.; Adaptive radiation therapy; 1997; Phys. Med. Biol.; 42:123-132.

*Primary Examiner*—Charles A Marmor, II
*Assistant Examiner*—Carrie Dorna

(57) ABSTRACT

A method and apparatus for planning a radiation therapy are disclosed. A radiation dose distribution is adapted on the basis of shape and position variations of the organs of interest determined from a comparison of a first image and a second image which were taken at different points of time during the radiation treatment process.

14 Claims, 1 Drawing Sheet

METHOD AND DEVICE FOR PLANNING A RADIATION THERAPY

CROSS REFERENCE TO RELATED APPLICATIONS

This application claims the benefit of U.S. provisional application Ser. No. 60/506,972 filed Sep. 29, 2003, and U.S. provisional application Ser. No. 60/584,833 filed Jun. 30, 2004 which are both incorporated herein by reference.

The disclosed devices and methods relate to the field of radiation therapy planning (RTP). In particular, the disclosed devices and methods relate to a method of planning a radiation therapy, to a radiation therapy planning device and to a computer program for a radiation therapy planning device.

Radiation Therapy Planning (RTP) may be carried out using a computed tomography (CT) image of a patient that is acquired prior to an actual radiation treatment of the patient. Radiation planning systems usually require data regarding contours of the target volume of a patient containing, for example, a tumour, and of the healthy, at-risk organs which have to be spared during dose delivery. Using this contour data, which are delineated by manual or semi-automatic contouring methods, a dose distribution is calculated for the structures of interest and the optimal parameters of radiation treatment beams are computed.

Dose calculations can lose accuracy during the treatment process because of shape and position changes of the organs occurring from certain physiological processes, such as bladder filling, increases or decrease of the tumour sizes, breathing, heartbeat, or other physiological processes.

It is an object of the presently dislosed devices and methods to provide for an improved radiation therapy planning.

A method of planning a radiation therapy is provided, wherein a dose distribution for a target volume comprising an object of interest is determined on the basis of a first image. Then, at least one of a shape and position variation of an object of interest in the target volume is determined on the basis of the first image and a second image. The dose distribution is then adjusted on the basis of the at least one of shape and position variation of the object of interest. The first and second images were taken at different points in time of a radiation treatment.

An initial dose distribution may be determined on the basis of a first image, which is, for example, taken before the start of the actual radiation treatment. Then, for example, after a plurality of dose deliveries or after a certain time or before a subsequent dose delivery, a second image is taken. Shape and/or position changes of the object of interest, such as the organs, between the first and second images, are determined. Then, the distribution is adjusted on the basis of the shape and/or position variation.

A radiation therapy planning may be provided allowing for an improved dose estimation for the target volume. This allows for an improved tumour control. Further, the dose calculation may be automatically adjusted taking into account changes to a patient's anatomy.

A first surface mesh is applied to the object of interest in the first image and is adapted to the surface of the object of interest, which results in a second surface mesh. This second surface mesh is applied to the object of interest in the second image and is adapted to the surface of interest in the second image. This adaptation of the second surface mesh to the object of interest results in a third surface mesh. Then, a difference between the second surface mesh and the third surface mesh is determined.

A method is provided for determining the contours of the object of interest in the target volume. By using such a surface mesh adaptation, an automatic organ delineation may be provided.

A volumetric model of the object of interest, such as one or more organs, is determined on the basis of the second surface mesh. Then, the volumetric model is deformed on the basis of the difference, for example, shape and/or position changes of the organs between the first image and the second image. The deformation of the volumetric model results in a deformed volumetric model. The shape and/or variation(s) of the object of interest is interpolated into the volumetric model. The difference, i.e., the shape and/or position variation of the object of interest is used as a boundary condition for the deformation of the volumetric model. At least one of shape and position variation of the object of interest is determined on the basis of the deformed volumetric model.

The dose calculation is adjusted, taking into account changes of the object of interest between the first and second image, for example, changes in the patient's anatomy occurring during the time between the first and second images.

A model of the biomechanical tissue-properties is taken into account for the deformation of the volumetric model. A combination of surface meshes and a biomechanical, volumetric model is used for a very accurate and automatic radiation therapy planning. In particular, the adapted surface meshes are used as a boundary condition for the deformation of the biomechanical, volumetric model.

A shape and/or position variation of the object of interest is determined. The object of interest may, for example, contain a plurality of organs, each having different mechanical characteristics. The biomechanical model takes these different mechanical characteristics into account when the shape and/or position variation of the object of interest determined on the basis of the surface meshes is used to deform the biomechanical, volumetric model accordingly. This allows a treating individual to more accurately take into account non-rigid changes occurring in the patent's anatomy during the radiation treatment. The first and second images may be computed tomography (CT) images. Alternatively, the procedure is possible with magnetic resonance imaging (MRI) images.

A radiation therapy planning device is provided comprising a memory for storing the first and second images and a processor performing a dose distribution adjustment on the basis of at least one of a shape and position variation of the object of interest between the first image and the second image. A radiation therapy planning device may be provided allowing for a fast and accurate radiation therapy planning which may be performed automatically. Changes in the patient's anatomy are taken into account for determining the dose distribution.

A computer program is provided for a radiation therapy planning device which allows for an automatic dose distribution determination by a combination of surface meshes applied to the object of interest in at least two subsequent images. By such a combination of a segmentation and a registration, an improved radiation therapy planning may be provided which may allow to reduce a dose applied to healthy (risk) organs. This computer program may be written in any suitable programming language; such as C++ and may be stored on a computer-readable device, such as a CD-ROM. However, the computer program may also be presented over a network, such as the Internet, from which it may be downloaded or run.

Devices and methods related to planning a radiation therapy for a patient are disclosed and discussed with reference to the following drawings.

Figure 1:
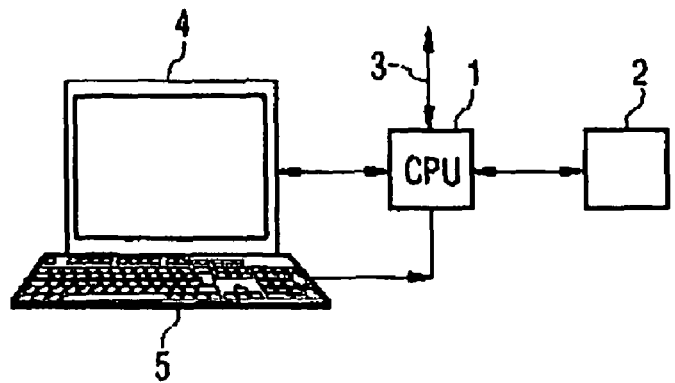
FIG. 1 is a schematic representation of a radiation therapy planning device adapted to execute a method as disclosed herein.

FIG. 1 shows a simplified schematic representation of a radiation therapy planning device. In FIG. 1, a Central Processing Unit (CPU) 1 is configured to execute instructions to carry out a method related to radiation therapy planning. CPU 1 may be a general purpose processor such as that found in a typical personal computer, or it may be an application-specific integrated circuit (ASIC). The instructions executed by CPU 1 assist a user in the planning of a radiation therapy with respect to an object of interest in a target volume. The target volume is usually an area within a patient containing a cancerous tumour or other structure that will be irradiated as part of the therapy being planned.

The target volume may comprise a plurality of other, smaller objects, such as different organs such as the bladder, the heart, or another organ. Usually, in cases where a radiation therapy is performed with respect to such target volumes, a tumour is located between or close to such organs. The object of most radiation therapies is usually to focus dosages of radiation onto the tumour while minimizing exposure to healthy at-risk organs adjacent to the tumour.

The CPU 1 is connected to a memory 2 for storing images. Memory 2 can be volatile memory such as dynamic random-access memory (DRAM), or a non-volatile memory device such as Flash memory or a disk drive. Other suitable devices capable of storing information for later retrieval and use may be used as the memory 2. In particular, in the memory 2, there are stored a first image taken at a first point in time of a radiation therapy process and a second image taken at a subsequent point in time. For example, the first image may be taken before the start of the radiation treatment. An initial radiation dose distribution is determined on the basis of information contained in this first image. Then, during the radiation treatment, for example, after a plurality of radiation treatments or before another immediate radiation treatment, a second image is created. Variations in the patient's anatomy, such as shape and/or position changes of the organs in the target volume, are determined from a comparison of the first image and the second image and the dose distribution is automatically adjusted to take into account noted changes in the patient's anatomy.

As may be taken from FIG. 1, the processor may, furthermore, be connected by a bus system 3 to a plurality of peripheral devices or input/output devices which are not depicted in FIG. 1. For example, the CPU 1 may be connected to a magnetic resonance (MR) device, an ultrasonic scanner, a plotter, a printer or other appropriate device via the bus system 3. Preferably, for radiation therapy planning, the CPU 1 is connected to a CT scanner that acquires the first and second images. More than two images may be used if necessary or desirable.

The CPU 1 is operatively connected to a display, such as a computer screen 4 for outputting the initial dose distribution and/or the adjusted dose distribution in a human-readable format. Furthermore, an input device such as keyboard 5 may be provided and operatively connected to the CPU 1, by which a user or operator may interact with the therapy planning device depicted in FIG. 1 or may input data necessary or desired for the radiation therapy planning.

Figure 2:
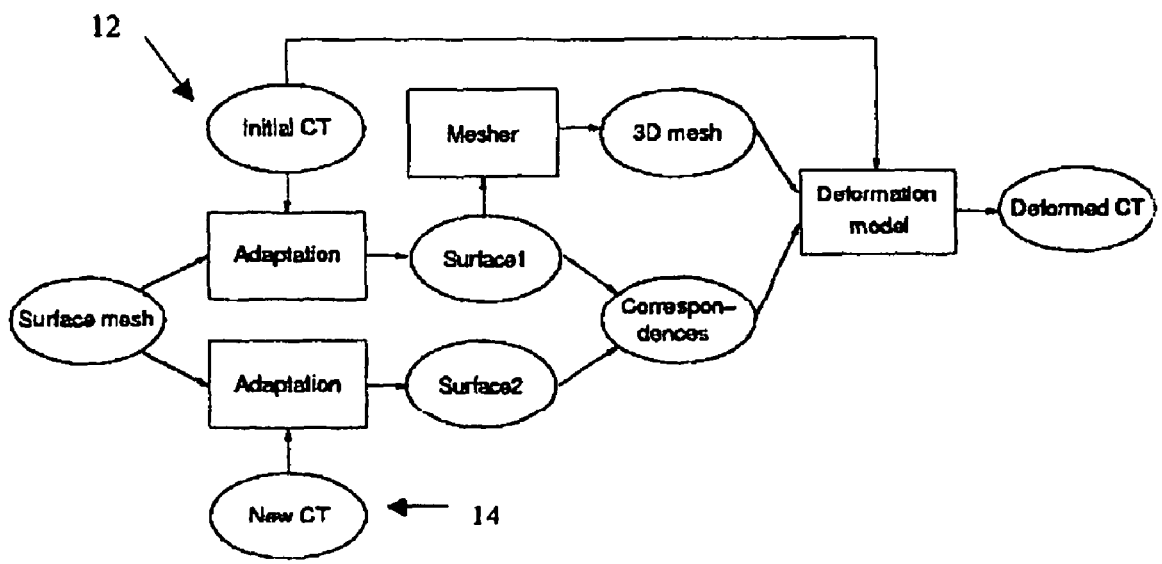
FIG. 2 is a flow diagram of a method of radiation therapy planning.

FIG. 2 is a flow diagram of a method of operating the radiation therapy planning device depicted in FIG. 1. The disclosed method of planning a radiation therapy may be embodied in a computer program, which may be written in any suitable programming language, such as C++ and may be stored on a computer-readable medium, such as a CD-ROM. However, the computer program according to the present invention may also be presented over a network, such as the Internet, from which the program may be downloaded.

The disclosed method takes into account the possibility that a dose distribution that was initially determined on the basis of a CT image taken before the actual start of the radiation therapy may need to be adjusted to accommodate changes in shape or position of organs due to certain physiological processes, for example, bladder filling, increase or decrease of the tumour size, breathing, heartbeat, or another process. Ideally, the dose distribution is individually adjusted for each day of treatment. The dose calculation is automatically adjusted taking into account changes in the patient's anatomy from one day to the next. For this adjustment, new CT images should be taken for each day of treatment.

In FIG. 2, two CT images are used for adjusting the dose distribution. The first CT image is referred to as initial CT image 12 and the second image is referred to as new CT image 14. Preferably, the initial CT image 12 is taken before the start of the radiation therapy treatment and new CT image 14 is then taken during the treatment process, for example, right before a subsequent radiation treatment.

Boundaries of a patient's organ structures in the target volume are delineated. The delineation of the organ boundaries in the initial CT image 12 may be performed manually or semi-automatically. Preferably, 3D surface models are used for performing an automated organ boundary delineation. A suitable process for performing a delineation is described in "Shape Constrained Deformable Models for 3D Medical Image Segmentation" by J. Weese et al, Proc. Information Processing in Medical Imaging (IPMI '01), at pages 380-387, Los Angeles, Calif., USA, June 2001, which is incorporated by reference.

In accordance with the application of 3D surface models, a surface mesh, such as a triangular mesh, is applied to the organs in the initial CT image 12. This process is sometimes referred to as adaption. It should be noted that instead of triangular meshes, it is also possible to use simplex or polygonal meshes or other suitable surface or shape models. Then, this surface mesh is adapted to the surface of the organs in the initial CT image 12 by energy minimization.

A deformable model is represented by a mesh. The mesh includes V vertices with coordinates $x_i$ and T triangles. An iterative process adapts the mesh to an image. Each iteration includes a step to detect a surface and a step to reconfigure the mesh. The reconfiguration is accomplished by minimizing the equation $$E = E_{ext} + \alpha E_{int}.$$

$E_{ext}$ represents external energy. This drives the mesh toward surface patches previously detected. $E_{int}$ represents internal energy. Internal energy restricts the flexibility of the mesh. $\alpha$ provides a weight on the relative influence of each term.

To detect a surface, a search is performed along the triangle normal $n_i$ to find the point $\tilde{x}_i$ (x-bar sub i) with a combination of features that includes $F_i(\tilde{x}_i)$ and distance $\delta j$ to the triangle's center $\hat{x}_i$ (x-caret sub i) such that:

$$\tilde{x}_i = \hat{x}_i + n_i \delta \arg \max_{j=-l,\ldots,l} \{F_i(x_i + n_i \delta j) - D\delta^2 j^2\}.$$

The profile length of the search is represented by l, δ is the distance between two successive points, and D controls the weighting of the distance information and feature value. A feature that can be used is $$F_i(x) = \pm n_i^t g(x) \frac{g_{max}(g_{max} + \|g(x)\|)}{(g_{max}^2 + \|g(x)\|^2)}$$

where the function g(x) is the image gradient at point x.

External energy represented as $$E_{ext} = \sum_{i=1}^{T} w_i(\bar{x}_i - \hat{x}_i)^2,$$

$$w_i = \max\{0, F_i(\tilde{x}_i) - D(\bar{x}_i - \hat{x}_i)^2\}$$

can be used. In this case, detected surface points directly attract the triangle centers of the mesh. To diminish the influence of attraction to false object boundaries, which may be frequently detected at the beginning of the adaption process, centers of the triangles can be attracted by planes that are perpendicular to the image gradient at $\tilde{x}_i$ (x-tilde sub i):

$$E_{ext} = \sum_{i=1}^{T} w_i \left( \frac{g(\bar{x}_i)}{\|g(\bar{x}_i)\|} (\bar{x}_i - \hat{x}_i) \right)^2$$

Internal energy is introduced into the shape model that is represented by a mesh of triangles such that $$m_i = m_i^0 + \sum_{k=1}^{M} p_k m_i^k; i = 1, \ldots, V$$

where $m_i^0$ represents vertex coordinates of the mean model. Variation of the coordinates associated with the M eigenmodes of the model is represented by $m_i^k$. Weights of the eigenmodes are represented by $p_k$. Difference vectors for the deformable model and the shape model are then compared with deviation penalization:

$$E_{int} = \sum_{i=1}^{V} \sum_{j \in N(i)} \left( x_i - x_j - \varepsilon R \left( m_i^0 - m_j^0 + \sum_{k=1}^{M} p_k(m_i^k - k_j^k) \right) \right)^2$$

where N(i) contains the neighbours of vertex i.

After or parallel to the determination of a surface mesh representing the shape and/or position of the organs in the initial CT image 12, a delineation of the boundaries of these organs is performed in the new CT image 14. Preferably, the segmentation result of the initial CT image, the surface mesh adapted to the organ surfaces in the initial CT image 12, is used as a starting mesh in the new CT image 14. Then, this starting mesh is adapted to the organ surfaces of the organs in the new CT image 14 by energy minimization as described above.

After the adaptation of the surface mesh to the organ surfaces in the new CT image 14, two surface meshes are known representing the organ surfaces in the initial CT image 12 and in the new CT image 14. The first mesh representing the organ surfaces in the initial CT image 12 is referred to in FIG. 2 as surface1 and the second mesh representing the surfaces of the organs in the new CT image 14 is referred to surface2 in FIG. 2. In a subsequent step, a difference between the surface1 and the surface2 is determined. In other words, correspondences between the surface1 and surface2 are determined. For this, the initial CT image 12 and the new CT image 14 or the surface1 and surface2 are brought into a common co-ordinate system. Because surface1 and surface2 were determined by using the same surface model, point correspondences between surface 1 and surface 2 may be determined easily.

A volumetric mesh is generated from the surface1 in the initial image. This volumetric mesh is now deformed using the point correspondences obtained from the comparison of surface1 and surface2. The deformation of the volumetric mesh is determined by taking into account mechanical properties of the organs, by using one or more biomechanical models. The use of biomechanical models is, for example, described in D. Yan et al, "A Method for Calculating Dose in a Deforming Organ," Int. J. Radiat. Oncol., Biol., Phys., 44, pages 665-675, 1999, which is hereby incorporated by reference.

An example for a simple and efficient biomechanical model is described in the following: Let V be a 3D domain occupied by the organ of interest and S be the organ boundary. A boundary value problem describing a linear elastic deformation of the organ can be formulated as:

$$\begin{cases} \int_V A(u) = f(x) & \text{in } V, \\ u(x) = \hat{u}(x) & \text{on } S. \end{cases}$$

In the above formula, A(u) denotes the operator of linear elasticity, as, for example, described in P. G. Ciarlet, "Mathematical Elasticity, Volume 1: Three-Dimensional Elasticity, volume 20 of Studies in Mathematics and its Applications." North-Holland, Amsterdam, 1988, which is hereby incorporated by reference. f(x) are the applied forces. u(x) denotes the displacement field, where û(x) are the prescribed displacements on the boundary determined by using the surface meshes. A discretization of the above formula on the volumetric mesh by the finite element method results in a linear system of equations. Prescribed displacements can be included into the system as boundary conditions to constrain the resulting volumetric deformation. According to an aspect of the present invention, these boundary conditions correspond to the point correspondences between the surface1 and surface2.

Elastic properties of particular tissues can be assigned to individual tetrahedra in the 3D mesh to more exactly simulate the elastic behaviour of an organ or organs. If the organ deformation is large and cannot be adequately described by the linear model, a non-linear elastic model in the form of incremental deformation may be applied.

As a result, advantageously, displacements of individual nodes inside the organ may be computed. During radiation treatment, dose estimation in the volume of interest can be performed taking into account variations or changes of the patient's anatomy based on these computed displacements. This estimation is then used to predict the dose delivery and helps to correct the initial treatment plan.

As described above, a combination of a segmentation and a registration is applied to take variations in the patient's anatomy during the radiation treatment into account to adjust the dose distribution and dose delivery estimation. This is achieved by combining a surface matching method with a biomechanical, volumetric model. In particular, the result of the surface method is used as boundary condition for the biomechanical, volumetric model.

Advantageously, due to the above method, the dose delivery during the treatment process may be monitored. For each point in time, where an image was taken, due to the above method, the precise dose distribution can be determined. In other words, for each relevant point in time of the treatment, and for each point of interest in the target volume (risk organs) the dose delivered can be determined. This may be done by summing the dose during each dose delivery to respective points.

The invention disclosed herein is defined by the claims read by a person of ordinary skill in the art in light of the disclosures made in the specification. Modifications of and alterations to the materials disclosed herein will occur to others upon reading and understanding of the preceding detailed description. It is intended that the invention be construed as including all such modifications and alterations insofar as they come within the scope of the appended claims or the equivalents thereof.

The invention claimed is:

1. A method of planning a radiation therapy, the method comprising the steps of:
   determining a dose distribution for a target volume on the basis of a first image;
   determining at least one of shape and position variation of a surface of an object of interest in the target volume between the first image and a second image, the first and second images being taken at different points in time of a radation process, including:
      applying a first surface mesh to the object of interest in the first image;
      performing a first adaptation of the first surface mesh to a surface of the object of interest in the first image resulting in a second surface mesh;
      applying the second surface mesh to the object of interest in the second image;
      performing a second adaptation of the second surface mesh to the surface of the object of interest in the second image resulting in a third surface mesh; and
      obtaining a difference between the second surface mesh and the third surface mesh;
   adjusting the dose distribution on the basis of the at least one of shape and position variation; and
   at least one of storing the adjusted dose distribution and displaying the adjusted dose distribution.

2. The method of claim 1 further comprising the steps of:
   generating a volumetric model of the object of interest on the basis of the second surface mesh; and
   deforming the volumetric model on the basis of the difference resulting in a deformed volumetric model.

3. The method of claim 2,
   wherein the difference is used as a boundary condition for the deformation of the volumetric model.

4. The method of claim 2,
   wherein the at least one of shape and position variation of the object of interest is determined on the basis of the deformed volumetric model.

5. The method of claim 2,
   wherein a biomechanical model is taken into account for the deformation of the volumetric model.

6. The method of claim 1, wherein the first and second images are computed tomography (CT) images.

7. The method of claim 1, wherein the second surface mesh and the third surface mesh result from applying the same surface model.

8. A radiation therapy planning device, comprising:
   a memory for storing a first image and a second image; and
   a processor for:
      applying a first surface mesh to the object of interest in the first image;
      performing a first adaptation of the first surface mesh to a surface of the object of interest in the first image resulting in a second surface mesh;
      applying the second surface mesh to the object of interest in the second image;
      performing a second adaptation of the second surface mesh to the surface of the object of interest in the second image resulting in a third surface mesh;
      obtaining a difference between the second surface mesh and the third surface mesh;
      generating a volumetric model of the object of interest on the basis of the second surface mesh;
      deforming the volumetric model on the basis of the difference resulting in a deformed volumetric model;
      determining a dose distribution for a target volume on the basis of the first image;
      determining at least one of shape and position variation of an object of interest in the target volume between the first image and the second image; and
      adjusting the dose distribution on the basis of the at least one of shape and position variation;
      wherein the first and second images were taken at different points in time of a radiation treatment process.

9. The radiation therapy planning device of claim 8,
   wherein the difference is used as a boundary condition for the deformation of the volumetric model; and
   wherein a biomechanical model is taken into account for the deformation of the volumetric model.

10. The radiation therapy planning device of claim 8, wherein the second surface mesh and the third surface mesh result from applying the same surface model.

11. A computer readable medium carrying a computer program for a radiation therapy planning device, wherein a processor of the radiation therapy device performs the following operation when the computer program is executed on the processor:
   determining a dose distribution for a target volume on the basis of a first image;
   applying a first surface mesh to the object of interest in the first image;
   performing a first adaptation of the first surface mesh to a surface of the object of interest in the first image resulting in a second surface mesh;
   applying the second surface mesh to the object of interest in the second image;
   performing a second adaptation of the second surface mesh to the surface of the object of interest in the second image resulting in a third surface mesh;
   obtaining a difference between the second surface mesh and the third surface mesh;
   generating a volumetric model of the object of interest on the basis of the second surface mesh;
   deforming the volumetric model on the basis of the difference resulting in a deformed volumetric model; and
   adjusting the dose distribution on the basis of the deformed volumetric model;
   wherein the first and second images were taken at different points in time of a radiation treatment process.

12. A method for adapting a dose distribution of a radiation therapy plan comprising:
adapting a first surface mesh to an object of interest in a first image resulting in a first adapted surface mesh;
adapting the first adapted surface mesh to the object of interest in a subsequent image resulting in a second adapted surface mesh;
deforming a volumetric model of the object of interest based on a difference between the first adapted surface mesh and the second adapted surface mesh; and
at least one of storing the deformed volumetric model and displaying the deformed volumetric model.

13. The method of claim 12, wherein the subsequent image is acquired prior to a radiation therapy treatment.

14. The method of claim 12, wherein the subsequent image is acquired prior to a predetermined interval of radiation therapy treatments.

* * * * *